United States Patent [19]

Cotteret et al.

[11] Patent Number: 4,725,283
[45] Date of Patent: Feb. 16, 1988

[54] DYEING COMPOSITIONS FOR KERATINIC FIBRES, BASED ON HALOGENATED META-PHENYLENEDIAMINES

[75] Inventors: Jean Cotteret, Limay; Alex Junino, Livry-Gargan; Gerard Lang, Saint Gratien, all of France

[73] Assignee: L'Oreal, Paris, France

[21] Appl. No.: 872,387

[22] Filed: Jun. 10, 1986

[30] Foreign Application Priority Data

Jun. 10, 1985 [LU] Luxembourg ............................ 85940

[51] Int. Cl.$^4$ .............................................. A61K 7/13
[52] U.S. Cl. ........................................... 8/429; 8/407; 8/408; 8/414; 8/415
[58] Field of Search .................... 8/407, 408, 409, 411, 8/414, 415, 429; 564/441, 367, 368, 369, 371

[56] References Cited

U.S. PATENT DOCUMENTS

| | | | |
|---|---|---|---|
| 3,555,584 | 1/1971 | Kalopissis et al. | 8/10.1 |
| 3,578,387 | 5/1971 | Zviak et al. | 8/407 |
| 3,632,292 | 1/1972 | Kalopissis et al. | 8/10.1 |
| 3,733,175 | 5/1973 | Alperin et al. | 8/414 |
| 4,155,934 | 5/1979 | Kalopissis et al. | 564/441 |
| 4,601,726 | 7/1986 | Grollier et al. | 8/414 |

FOREIGN PATENT DOCUMENTS

| | | |
|---|---|---|
| 0132568 | 6/1984 | European Pat. Off. |
| 1619615 | 9/1970 | Fed. Rep. of Germany . |
| 1127080 | 9/1968 | United Kingdom . |
| 2099838A | 12/1982 | United Kingdom . |
| 2164656A | 3/1986 | United Kingdom . |

*Primary Examiner*—Prince E. Willis
*Assistant Examiner*—Linda D. Skaling
*Attorney, Agent, or Firm*—Fleit, Jacobson, Cohn & Price

[57] ABSTRACT

The invention relates to dyeing compositions for direct dyeing of keratinic fibres, containing, in a cosmetically acceptable medium:

(a) at least one yellow or green-yellow dye corresponding to the formula (I):

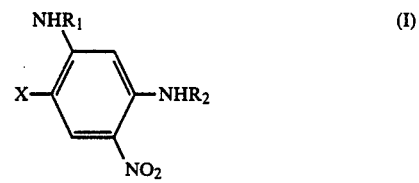

in which $X = Cl$, $Br$, $F$, and $R_1$ and $R_2$ denote, independently of each other, hydrogen, alkyl, hydroxyalkyl, or alkylaminoalkyl in which the aminoalkyl group may be mono- or disubstituted provided that $R_1$ and $R_2$ do not simultaneously denote a hydrogen atom, and (b) at least one blue or violet dye corresponding to the formula:

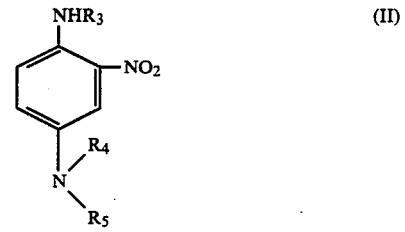

in which $R_3$ denotes a hydrogen atom or an alkyl, monohydroxyalkyl, polyhydroxyalkyl or alkoxyalkyl radical and $R_4$ and $R_5$ have separately the same meanings as $R_3$ but cannot denote a hydrogen atom.

13 Claims, No Drawings

DYEING COMPOSITIONS FOR KERATINIC FIBRES, BASED ON HALOGENATED META-PHENYLENEDIAMINES

The present invention relates to new compositions for dyeing keratinic fibres and especially human hair, containing certain halogenated meta-phenylenediamines, and to the use of these compositions for dyeing keratinic fibres.

In the field of hair dyeing it is well known to use what are known as oxidation dyes, which produce shades which have good covering power and which are very fast. In general, oxidative dyeing makes use of oxidizing agents which can damage hair when such dyes are applied very frequently. Furthermore, a dividing line is observed between the dyed ends and middle lengths and the undyed roots, which is due to fresh hair growth between two dyeing operations.

There is also a demand for dyes of possibly lesser fastness and requiring more frequent application. Dyes known as "direct" dyes, that is to say not requiring the use of an oxidative mechanism, have been used for this purpose.

By virtue of the variety of possible substituents, such dyes enable a wide range of shades to be covered, from yellow, via red, to blue.

These direct dyes, among which nitrobenzene dyes may be mentioned, are very effective and, in general, well tolerated. To produce natural colours or colours with natural highlights, use is made of mixtures of blue or violet and yellow or green-yellow dyes.

However, while being of interest in themselves, these blue or violet dyes have the disadvantage of being selective. The selectivity of a dye is the name given to the difference in the colour strength of the latter on the hair fibre according to whether the latter is more or less sensitized either by a treatment such as a bleaching, a permanent waving, or by atmospheric agents, especially where the ends are concerned.

This problem of selectivity results in an imbalance in the shades or in the highlights according to the degree of sensitization of the hair to which the composition containing a mixture of dyes, especially blue or violet and yellow or green-yellow, is applied.

A highlight which is excessively purplish-blue at the ends and a highlight which is excessively matt over the lengths, or the converse, are observed, in fact, depending on the balance of the dyes chosen by the formulator, in the case of the mixtures of the prior art and of hair having regions of unequal sensitization, for example over the lengths and at the ends.

The Applicant has now found that it is possible to obtain natural shades with better balance over the entire length of the hair by combining two individual groups of blue or violet nitro dyes and of yellow or green-yellow dyes.

Furthermore, this combination shows good resistance to washing and to light and makes it possible to preserve a natural shade which is balanced over the entire length of the hair between two dyeing operations.

Consequently, a subject of the invention consists of new dyeing compositions employing a particular group of yellow or green-yellow halogenated nitrobenzene dyes with blue or violet nitrobenzene dyes.

Another subject of the invention consists of the dyeing process using such compositions.

Other subjects of the invention will become apparent in the reading of the description of the examples which follow.

The dyeing composition for keratinic fibres and especially for human hair, in accordance with the invention, is essentially characterized in that it contains (a) at least one yellow or green-yellow nitrobenzene dye corresponding to the formula:

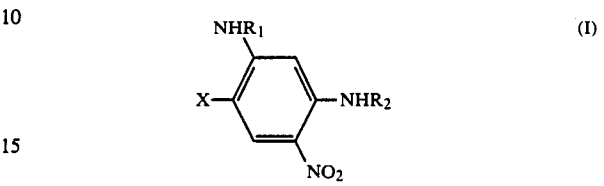

in which X=Br, Cl or F, $R_1$ and $R_2$ denote, independently of each other, hydrogen, alkyl, hydroxyalkyl, or alkylaminoalkyl in which the amino group may be mono- or disubstituted, provided that $R_1$ and $R_2$ do not simultaneously denote a hydrogen atom, and (b) at least one blue or violet nitrobenzene dye.

The blue or violet nitro dyes which are particularly preferred in accordance with the invention correspond to the formula (II)

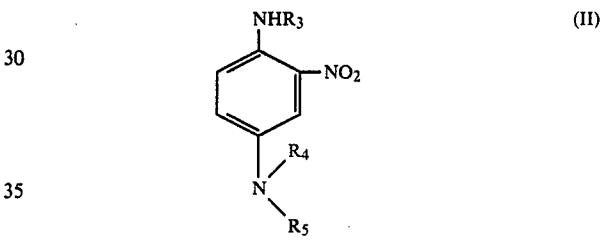

in which $R_3$ denotes a hydrogen atom, an alkyl radical, a monohydroxyalkyl, polyhydroxyalkyl or alkoxyalkyl radical and $R_4$ and $R_5$ have independently the same meanings as $R_3$, but cannot denote a hydrogen atom.

The alkyl radicals in the above formulae I and II preferably contain 1 to 4 carbon atoms and the substituents of the amino group are preferably $C_1$-$C_4$ alkyl, hydroxyalkyl and similar groups.

The following compounds are preferably used among the dyes of formula (I):

2-N-β-hydroxyethylamino-4-N-β-hydroxyethylamino-5-chloronitrobenzene,

2-N-methylamino-4-amino-5-fluoronitrobenzene,

2-N-β-hydroxyethylamino-4-amino-5-chloronitrobenzene,

2-N-propylamino-4-amino-5-chloronitrobenzene,

2-N-β-hydroxyethylamino-4-amino-5-bromonitrobenzene, 2-amino-4-N-β-hydroxyethyl-5-chloronitrobenzene, 2-N-β-aminoethylamino-4-amino-5-chloronitrobenzene, 2-N-methylamino-4-amino-5-fluoronitrobenzene, 2-N-β-hydroxyethylamino-4-amino-5-bromonitrobenzene, 2-β-N,N-diethylaminoethylamino-4-amino-5-chloronitrobenzene, 2-N-β-aminoethylamino-4-N-β-hydroxyethylamino-5-chloronitrobenzene, 2,4-bis-N-γ-hydroxypropylamino-5-chloronitrobenzene, 2,4-bis-N-β-hydroxypropylamino-5-chloronitrobenzene, and more particularly the compound 2-N-β-hydroxyethylamino-4-N-β-hydroxyethylamino-5-chloronitrobenzene.

The abovementioned dyes are preferably used with the following blue or violet nitrobenzene dyes of formula (II):

2-N-methylamino-5-N,N-bis(β-hydroxyethyl)aminonitrobenzene, 2-N-methylamino-5-(N-methyl-N-β-hydroxyethyl)aminonitrobenzene, 2-N-β-hydroxyethylamino-5-N,N-bis-β-hydroxyethylaminonitrobenzene, 2-N-β-hydroxyethylamino-5-(N-methyl-N-β-hydroxyethyl)aminonitrobenzene, 2-N-β-hydroxypropylamino-5-N,N-bis-β-hydroxyethylaminonitrobenzene, 2-N-methylamino-5-(N-methyl-N-β,γ-dihydroxypropyl)aminonitrobenzene, 2-amino-5-N,N-bis-β-hydroxyethylaminonitrobenzene, 2-N-β-hydroxyethylamino-5-(N-ethyl-N-β-hydroxyethyl)aminonitrobenzene, 2-N-β,γ-dihydroxypropylamino-5-(N-methyl-N-β-hydroxyethyl)aminonitrobenzene and 2-β-methoxyethylamino-5-N,N-bis-β-hydroxyethylaminonitrobenzene.

The dyes of formula (I) are present in the dye compositions according to the invention in proportions which are preferably between 0.01 and 2% by weight relative to the total weight of the composition. The violet or blue dyes of above formula (II) are preferably present in proportions of between 0.01 and 5% by weight relative to the total weight of the composition.

Although the combination of the dyes of formula (I) and the dyes of formula (II) as they are defined above makes it possible to obtain a balanced natural shade, it is possible, of course, to vary the tints of this shade by using, in addition to the dyes of formulae (I) and (II), other nitrobenzene dyes, or else azo, aminoanthraquinone or metal-containing dyes, triarylmethane derivatives or indoamino dyes. These other direct dyes may be present as between 0.001 and 10% by weight of the total weight of the composition.

Among other nitrobenzene dyes which may be used in the compositions according to the invention there may be mentioned the dyes belonging to the class of nitropara-phenylenediamines, nitroaminophenols, nitroaminoalkoxybenzenes and nitroaminohydroxyalkoxybenzenes. Dyes which are especially capable of being used in the compositions according to the invention are chosen from the following dyes:

2-amino-5-N-methylaminonitrobenzene, 2,4-diaminonitrobenzene, 3,4-diaminonitrobenzene, 2,5-diaminonitrobenzene, 3-amino-4-hydroxynitrobenzene, 3-hydroxy-4-aminonitrobenzene, 2-hydroxy-5-aminonitrobenzene, 2-amino-5-hydroxynitrobenzene, 2-amino-3-hydroxynitrobenzene, 2-amino-5-N-β-hydroxyethylaminonitrobenzene, 2-N-β-hydroxyethylamino-5-hydroxynitrobenzene, 3-methoxy-4-N-β-hydroxyethylaminonitrobenzene, 2-N-methylamino-4-(β-hydroxyethoxy)nitrobenzene, 2-amino-3-methylnitrobenzene, 2-N-(β-hydroxyethyl)amino-5-aminonitrobenzene, 2-amino-4-chloro-5-N-(β-hydroxyethyl)aminonitrobenzene, 2-amino-4-methyl-5-N-(β-hydroxyethyl)aminonitrobenzene, 2-amino-4-methyl-5-N-methylaminonitrobenzene, 2-N-(β-hydroxyethyl)amino-5-methoxynitrobenzene, 2-amino-5-(β-hydroxyethoxy)nitrobenzene, 2-N-(β-hydroxyethyl)aminonitrobenzene, 3-amino-4-N-(β-hydroxyethyl)aminonitrobenzene, 3-(β-hydroxyethoxy)-4-N-(β-hydroxyethyl)aminonitrobenzene, 2-N-methylamino-4-(β,γ-dihydroxypropoxy)nitrobenzene, 2-N-(β-hydroxyethyl)amino-5-(β-hydroxyethoxy)nitrobenzene, 2-N-(β-hydroxyethyl)amino-5-(β,γ-dihydroxypropoxy)nitrobenzene, 3-hydroxy-4-N-(β-hydroxyethyl)aminonitrobenzene, 3-N-(βhydroxyethyl)amino-4-N-(β-hydroxyethyl)aminonitrobenzene, 2-amino-4-methyl-5-N-(β,γ-dihydroxypropyl)aminonitrobenzene, 2-amino-4-methyl-5-hydroxynitrobenzene, 2-N-(β-aminoethyl)amino-4-methoxynitrobenzene, 2-N-(β-aminoethyl)aminonitrobenzene, 2-N-(β-aminoethyl)amino-5-N-(β-hydroxyethyl)aminonitrobenzene, 2-amino-4-methyl-5-N-(β-aminoethyl)aminonitrobenzene, and 2-amino-4-chloro-5-N-(β-hydroxyethyl)aminonitrobenzene.

The cosmetically acceptable medium used in the compositions according to the invention may consist of water or a mixture with organic solvents which are acceptable from the standpoint of cosmetics, such as, more particularly, alcohols such as ethyl alcohol, isopropyl alcohol, benzyl alcohol and phenylethyl alcohol, or glycols or glycol ethers such as, for example, ethylene glycol and its monomethyl, monoethyl and monobutyl ethers, propylene glycol, butylene glycol, dipropylene glycol and diethylene glycol alkyl ethers such as, for example, diethylene glycol monoethyl ether or monobutyl ether, in concentrations of between 0.5 to 20% by weight and preferably between 2 and 10% by weight relative to the total weight of the composition.

These compositions may also contain fatty amides such as mono- and diethanolamides of acids derived from copra, of lauric acid or of oleic acid in concentrations of between 0.05 and 10% by weight.

In their preferred form, the compositions according to the invention may contain anionic, cationic, nonionic or amphoteric surface-active agents or mixtures thereof. These surface-active agents are present in the composition in proportions which are advantageously between 0.1 and 50% by weight and preferably between 1 and 20% by weight relative to the total weight of the composition.

Among the surface-active agents those which may be mentioned more particularly are anionic surface-active agents used by themselves or mixed, such as, especially, the alkali metal salts, the magnesium salts, the ammonium salts, the amine salts and the alkanolamine salts of alkylsulphates, alkylethersulphates, alkylamidesulphates, ethoxylated or otherwise, of alkylsulphonates, of alkylamidesulphonates, of alpha-olefinsulphonates, of alkylsulphoacetates, fatty acids such as lauric, myristic, oleic, ricinoleic, palmitic and stearic acids, acids from copra oil or from hydrogenated copra oil, and polyglycol ether carboxylic acids.

The alkyl radicals in these compounds preferably consist of a linear chain containing from 12 to 18 carbon atoms.

As cationic surface-active agents there may be mentioned, more particularly, fatty amine salts, quaternary ammonium salts such as alkyldimethylbenzylammonium, alkyltrimethylammonium, alkyldimethylhydroxyethylammonium and dimethyldialkylammonium chlorides and bromides, alkylpyridinium salts and imidazoline salts. The alkyl groups in the abovementioned quaternary ammonium derivatives are long-chain groups containing preferably between 12 and 18 carbon atoms.

Amine oxides may also be mentioned among these compounds of a cationic nature.

Among amphoteric surface-active agents there may be particularly mentioned alkylamino(mono- and di-)propionates, betaines such as alkylbetaines, N-alkylsulphobetaines and N-alkylaminobetaines, the alkyl radical containing between 1 and 22 carbon atoms, and cycloimidiniums such as alkylimidazolines.

The compositions according to the invention may be thickened by means of thickening agents such as, for example, sodium alginate, gum arabic, guar gum, xanthane gum, cellulose derivatives such as methyl cellulose, hydroxyethyl cellulose, hydroxypropyl methyl cellulose, sodium salts of carboxymethyl cellulose and acrylic acid polymers. It is also possible to use inorganic thickening agents such as bentonite. These thickening agents are used by themselves or mixed and are preferably present in proportions between 0.1 and 5% by weight relative to the total weight of the composition and, advantageously, between 0.5 and 3% by weight.

The dye compositions according to the invention may be formulated at acid, neutral or alkaline pH values which can vary between 4 and 10.5 and preferably between 6 and 10. Among the alkalifying agents which may be used there may be mentioned alkanolamines and alkali metal or ammonium hydroxides and carbonates. The acidifying agents which may be used are, for example, lactic acid, acetic acid, tartaric acic, phosphoric acid, hydrochloric acid and citric acid.

Obviously, that these compositions may contain various adjuvants usually employed in cosmetic compositions, such as antioxidants, perfumes, sequestering agents, film-forming agents, processing agents, dispersing agents, hair-conditioning agents, preserving agents and opacifying agents.

The dye composition according to the invention may be presented in forms which are usually employed for hair dyeing, such as thickened or gelled liquid, cream, aerosol foam or any other suitable form for performing a hair-dyeing operation.

The process for dyeing keratinic fibres, especially human hair, which forms another subject of the invention is essentially characterized in that the dye composition defined above is allowed to act on dry or wet keratinic fibres.

For example, the composition may be applied in the form of a lotion and dried without an intermediate rinsing.

Another method of use may consist in applying the dye composition to the keratinic fibres for an application period varying between 3 and 60 minutes, and preferably between 5 and 45 minutes, rinsing, washing if appropriate, rinsing again and drying.

The dye compositions may be applied to various natural or dyed, permanent-waved or unwaved, strongly or slightly bleached and, if appropriate, permanent-waved hair.

The following examples are intended to illustrate the invention without, however, being of a limited nature.

EXAMPLES OF PREPARATION

Example A

Preparation of 2,5-dichloro-4-nitroaniline of formula

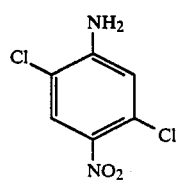

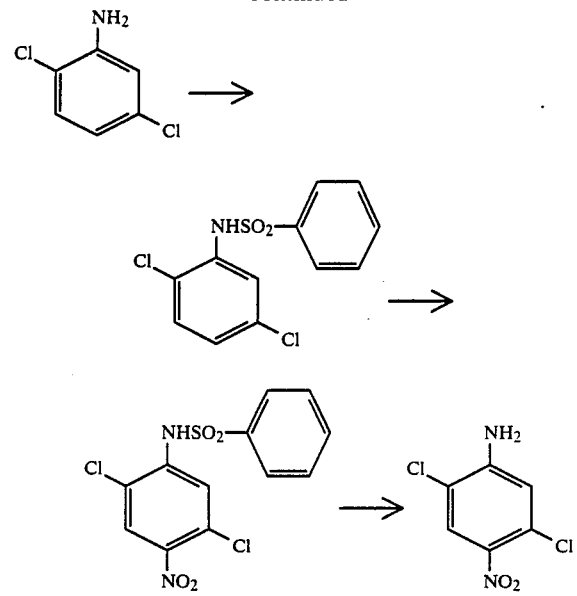

1st stage

Preparation of 2,5-dichloro-N-benzenesulphonylaniline 1 mole (162 g) of 2,5-dichloroaniline is dissolved in 650 ml of pyridine. 1.1 mole (138 ml) of benzenesulphonyl chloride is added, while the temperature is maintained between 35° C. and 45° C. After 2 hours' heating, the reaction mixture is poured into 4 kg of water and ice containing 550 ml of concentrated hydrochloric acid. The precipitate formed in this manner is filtered off and washed with water. Treatment with N sodium hydroxide solution produces an insoluble material which is separated off by filtration and the expected product precipitates when the filtrate is neutralized. It melts at 132° C.

2nd stage

Preparation of 2,5-dichloro-4-nitro-4-N-benzenesulphonylaniline

To 825 ml of acetic acid diluted with an equal volume of water are added: 2.8 g of sodium nitrite, 0.41 mole (125 g) of 2,5-dichloro-N-benzenesulphonylaniline prepared in the previous stage and 2.44 moles (102 ml) of nitric acid (d=1.52). The reaction mixture is heated to reflux for 1 hour. After the reaction mixture has cooled, the expected product is filtered off. After washing with water followed by recrystallization from acetic acid, it melts at 180° C.

3rd stage

Preparation 2,5-dichloro-4-nitroaniline 0.44 mole (154 g) of 2,5-dichloro-4-nitro-N-benzenesulphonylaniline prepared in the previous stage is suspended in 600 ml of concentrated sulphuric acid. After 24 hours' stirring at ambient temperature the reaction mixture is poured onto 5 kg of ice. The expected product precipitates. After filtering, washing to neutrality and drying, it melts at 156° C.

Analysis of the product obtained gives the following results:

| Analysis | Calculated for $C_6H_4N_2O_2Cl_2$ | Found |
|---|---|---|
| C | 34.78 | 34.62 |
| H | 1.93 | 1.98 |
| N | 13.53 | 13.40 |
| O | 15.46 | 15.66 |
| Cl | 34.30 | 34.24 |

EXAMPLE B

Preparation of 2,5-dibromo-4-nitroaniline (intermediate) of formula

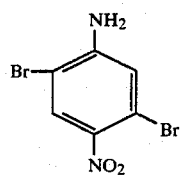

The operating procedure is identical to that described for 2,5-dichloro-4-nitroaniline.

1st stage

Preparation of 2,5-dibromo-N-benzenesulphonylaniline 0.175 mole (44 g) of 2,5-dibromoaniline is dissolved in 200 ml of pyridine and 0.2 mole (25 ml) of benzenesulphonyl chloride is added, while the temperature is maintained between 30° C. and 40° C. After 1 hour at 35° C. the reaction mixture is poured into 1.5 kg of ice and water containing 150 ml of concentrated hydrochloric acid. The precipitate thus obtained is filtered off. After treatment with N sodium hydroxide solution an insoluble material is obtained which is removed by filtration; the expected product crystallizes from the filtrate after neutralization. Recrystallized from acetic acid, it melts at 141° C.

2nd stage

Preparation of 2,5-dibromo-4-nitro-N-benzenesulphonylaniline

To 250 ml of acetic acid, diluted with 130 ml of water, are added: 1.5 g of sodium nitrite, 0.13 mole of 2,5-dibromo-N-benzenesulphonylaniline prepared in the previous stage and 0.78 mole (32.5 ml) of nitric acid (d=1.52). The reaction mixture is heated for 1 hour at 90° C. The reaction mixture, cooled beforehand, is poured onto 1 kg of ice and the expected product precipitates. It is filtered off, washed to neutrality and then recrystallized from acetic acid; it melts at 148° C.

3rd stage

Preparation of 2,5-dibromo-4-nitroaniline 15 ml of water are added, with due care, to 115 ml of concentrated sulphuric acid; the temperature rises to 70° C. 0.105 mole (46 g) of 2,5-dibromo-4-nitro-N-benzenesulphonylaniline are then added. The temperature is maintained at 70°-78° C. for 2 hours. The reaction mixture is poured into 1 kg of ice and water; the expected product precipitates. After filtration and washing to neutrality the product is recrystallized from 450 ml of ethanol. It melts at 178° C.

Analysis of the product obtained gives the following results:

| Analysis | Calculated for $C_6H_4N_2O_2Br_2$ | Found |
|---|---|---|
| C | 24.35 | 24.40 |
| H | 1.36 | 1.34 |
| N | 9.47 | 9.48 |
| O | 10.81 | 10.52 |
| Br | 54.00 | 53.86 |

EXAMPLE C

Preparation of 2,5-difluoro-4-nitroaniline (intermediate compound)

The operating procedure is identical to that described for 2,5-dichloronitroaniline.

1st stage

Preparation of the 2,5-difluoro-N-benzenesulphonylaniline 0.194 mole (25 g) of 2,5-difluoroaniline is added to 125 ml of pyridine. 0.2 mole (25.5 ml) of benzenesulphonyl chloride is added, while the temperature is between 35° C. and 45° C. The temperature is maintained at 40° C. for 1 hour after the addition is completed, and then the reaction mixture is poured onto 1 kg of ice and water to which 100 ml of concentrated hydrochloric acid have been added. The expected product precipitates. After filtration and washing, it is treated with a normal sodium hydroxide solution in order to remove insoluble material. The soda-containing filtrate is neutralized with concentrated hydrochloric acid. The expected product, which has precipitated, is filtered off, washed to neutrality and recrystallized from acetic acid. It melts at 115° C.

2nd stage

Preparation of 2,5-difluoro-4-nitro-N-benzenesulphonylaniline

To 310 ml of acetic acid diluted with 160 ml of water are added: 1.5 g of sodium nitrite, 0.16 mole (42 g) of 2,5-difluoro-N-benzenesulphonylaniline prepared in the previous stage and 0.94 mole (39 ml) of nitric acid (d=1.52). The reaction mixture is heated to 96° C. for 1 hour. After cooling it is poured onto 1 kg of ice and water. The expected product precipitates. After being filtered off and washed to neutrality it is recrystallized from 250 ml of acetic acid; it melts at 176° C.

3rd stage

Preparation of 2,5-difluoro-4-nitroaniline 10 ml of water are added with due care to 75 ml of concentrated sulphuric acid; the temperature rises to 70° C. 0.105 mole (33 g) of 2,5-difluoro-4-nitro-N-benzenesulphonylaniline prepared in the previous stage is then added. The temperature is maintained at 70° C. for 2 hours. The reaction mixture is poured onto 1 kg of ice and water and the expected product precipitates. After filtration and washing to neutrality the product is recrystallized from 100 ml of 96° ethanol. It melts at 153° C.

Analysis of the product obtained gives the following results:

| Analysis | Calculated for $C_6H_4N_2O_2F_2$ | Found |
| --- | --- | --- |
| C | 41.39 | 41.17 |
| H | 2.31 | 2.31 |
| N | 16.09 | 16.19 |
| F | 21.82 | 21.87 |

EXAMPLE D

Preparation of
2-N-propylamino-4-amino-5-chloronitrobenzene

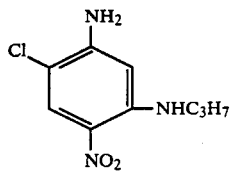

0.025 mole (5.14 g) of 2,5-dichloro-4-nitroaniline (compound A) and 15 ml of propylamine are heated to 120° C. in 15 ml of diethylene glycol dimethyl ether.

After 5 hours' heating, the reaction mixture is diluted with 150 ml of iced water.

The precipitate is filtered off and, after washing and drying, is recrystallized from 25 ml of toluene. It melts at 121° C.

Analysis of the product obtained gives the following results:

| Analysis | Calculated for $C_9H_{12}N_3O_2Cl$ | Found |
| --- | --- | --- |
| C | 47.06 | 46.87 |
| H | 5.27 | 5.26 |
| N | 18.30 | 18.23 |
| O | 13.93 | 13.86 |
| Cl | 15.44 | 15.71 |

EXAMPLE E

Preparation of
2-N-β-hydroxyethylamino-4-amino-5-chloronitrobenzene

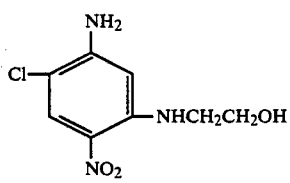

0.02 mole (4.14 g) of 2,5-dichloro-4-nitroaniline (compound A) is heated in 20 ml of ethanolamine on a steam bath.

After two hours' heating, the reaction mixture is diluted with 150 ml of iced water. The precipitate obtained is filtered off, washed with water and dried under vacuum. After recrystallization from acetic acid it melts at 188° C.

Analysis of the product gives the following results:

| Analysis | Calculated for $C_8H_{10}N_3O_3Cl$ | Found |
| --- | --- | --- |
| C | 41.48 | 41.34 |
| H | 4.35 | 4.39 |
| N | 18.14 | 18.18 |
| O | 20.72 | 20.76 |
| Cl | 15.31 | 15.26 |

EXAMPLE F

Preparation of
2-N-β-aminoethylamino-4-amino-5-chloronitrobenzene

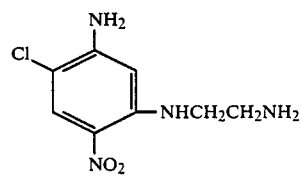

0.02 mole (4.14 g) of 2,5-dichloro-4-nitroaniline (compound A) are heated in 20 ml of ethylenediamine on a steam bath. Heating is continued for 1 hour. After the reaction mixture has been diluted with 150 ml of iced water, the precipitate is filtered off, washed and dried under vacuum.

After recrystallization from ethanol, it melts at 168° C.

Analysis of the product obtained gives the following results:

| Analysis | Calculated for $C_8H_{11}N_4O_2Cl$ | Found |
| --- | --- | --- |
| C | 41.66 | 41.50 |
| H | 4.81 | 4.84 |
| N | 24.29 | 24.41 |
| O | 13.87 | 14.05 |
| Cl | 15.37 | 15.25 |

EXAMPLE G

Preparation of
2-N-methylamino-4-amino-5-fluoronitrobenzene

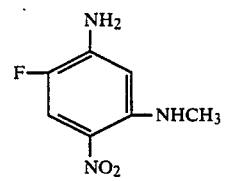

To 25 ml of ethanol are added 25 ml of a 40% strength solution of methylamine in water and 0.033 mole (6 g) of 2,5-difluoro-4-nitroaniline (compound C).

After 6 hours' stirring at ambient temperature the reaction mixture is cooled. The precipitate of the expected product is isolated by filtration. After recrystallization from dioxane, it melts at 213° C.

Analysis of the product obtained gives the following results:

| Analysis | Calculated for $C_7H_8N_3O_2F$ | Found |
| --- | --- | --- |
| C | 45.41 | 45.18 |

| Analysis | Calculated for C₇H₈N₃O₂F | Found |
|---|---|---|
| H | 4.35 | 4.38 |
| N | 22.61 | 22.72 |
| F | 10.26 | 10.16 |

EXAMPLE H

Preparation of 2-N-β-hydroxyethylamino-4-amino-5-bromonitrobenzene

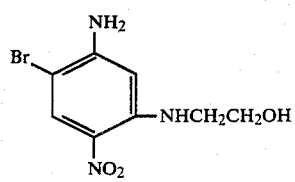

12 ml of ethanolamine are added to 15 ml of 96° ethanol, followed by 0.02 mole (5.92 g) of 2,5-dibromo-4-nitroaniline (compound B). The mixture is heated for 6 h 30 min in refluxing alcohol. After cooling and dilution of the reaction mixture with 100 ml of iced water, the expected product precipitates.

After recrystallization from acetonitrile, it melts at 174° C.

Analysis of the product obtained gives the following results:

| Analysis | Calculated for C₈H₁₉N₃O₃Br | Found |
|---|---|---|
| C | 34.80 | 35.03 |
| H | 3.65 | 3.70 |
| N | 15.22 | 15.27 |
| O | 17.38 | 17.34 |
| Br | 28.94 | 28.86 |

EXAMPLE I

Preparation of 2-amino-4-β-hydroxyethylamino-5-chloronitrobenzene

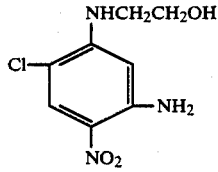

0.11 mole (22.8 g) of 4,5-dichloro-2-nitroaniline is added to a solution of 0.55 mole (33.3 ml) of ethanolamine in 70 ml of dioxane. The reaction mixture is heated for 6 hours in refluxing dioxane. After dilution with water and neutralization with concentrated hydrochloric acid, the expected product precipitates.

After recrystallization from absolute ethanol, it melts at 176° C.

Analysis of the product obtained gives the following results:

| Analysis | Calculated for C₈H₁₀N₃O₃Cl | Found |
|---|---|---|
| C | 41.48 | 41.65 |
| H | 4.35 | 4.43 |
| N | 18.14 | 18.05 |
| O | 20.72 | 20.49 |
| Cl | 15.31 | 15.48 |

EXAMPLE K

Preparation of 2-β-aminoethylamino-4-β-hydroxyethylamino-5-chloronitrobenzene

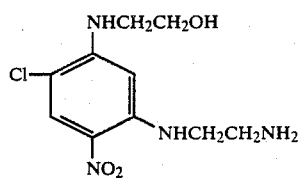

1st stage

Preparation of 4,5-dichloro-2-nitro-N-β-aminoethylaniline

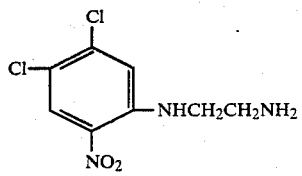

0.13 mole (30.6 g) of 2,4,5-trichloronitrobenzene is added to a solution of 78 g of ethylenediamine in 100 ml of 96° ethanol and 117 ml of water. After heating under reflux for 1 h 30 min, the reaction mixture is cooled. After dilution with iced water, the expected product precipitates. It melts as 84° C.–87° C.

2nd stage

Preparation of 2-chloro-5-β-aminoethylamino-4-nitro-N-(β-hydroxyethyl)aniline 0.04 mole (10 g) of 4,5-dichloro-2-nitro-N-β-aminoethylaniline prepared in the 1st stage is heated in 40 ml of monoethanolamine for 30 minutes to 100° C. The reaction mixture is diluted with 450 ml of iced water. An impurity is precipitated by adding hydrochloric acid and is removed by filtration. The filtrate is made alkaline with concentrated sodium hydroxide solution. The expected product precipitates. After filtration and drying, it is purified as its hydrochloride before being recrystallized from alcohol. It melts at 160° C.

Analysis of the product obtained gives the following results:

| Analysis | Calculated for C₁₀H₁₅N₄O₃Cl | Found |
|---|---|---|
| C | 43.72 | 43.81 |
| H | 5.50 | 5.51 |
| N | 20.39 | 20.38 |
| O | 17.47 | 17.42 |

| Analysis | Calculated for $C_{10}H_{15}N_4O_3Cl$ | Found |
|---|---|---|
| Cl | 12.91 | 12.84 |

EXAMPLE L

Preparation of 2,4-bis-N-β-hydroxyethylamino-5-chloronitrobenzene

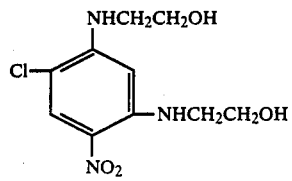

0.1 mole (22.6 g) of 2,4,5-trichloronitrobenzene is heated in 82 ml of ethanolamine on a steam bath for 3 hours. After cooling and dilution with iced water, the expected product precipitates.

After recrystallization from dioxane, it melts at 171° C.

Analysis of the product obtained gives the following results:

| Analysis | Calculated for $C_{10}H_{14}N_3O_4Cl$ | Found |
|---|---|---|
| C | 43.55 | 43.49 |
| H | 5.08 | 5.09 |
| N | 15.24 | 15.41 |
| O | 23.23 | 23.04 |
| Cl | 12.88 | 12.86 |

EXAMPLE M

Preparation of 2-β-hydroxyethylamino-4-amino-5-bromonitrobenzene

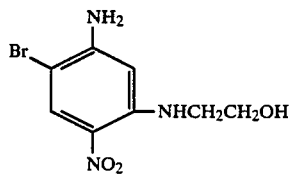

0.02 mole (5.92 g) of 2,5-dibromo-4-nitroaniline (compound B) is added to 15 ml of 96° ethanol to which 12 ml of ethanolamine have been added. The mixture is heated in refluxing alcohol for 6 h 30 min. After cooling and dilution of the reaction mixture with 100 ml of iced water, the expected product precipitates.

After recrystallization from acetonitrile, it melts at 174° C.

Analysis of the product obtained gives the following results:

| Analysis | Calculated for $C_8H_{10}N_3O_3Br$ | Found |
|---|---|---|
| C | 34.80 | 35.03 |
| H | 3.65 | 3.70 |
| N | 15.22 | 15.27 |
| O | 17.38 | 17.34 |

| Analysis | Calculated for $C_8H_{10}N_3O_3Br$ | Found |
|---|---|---|
| Br | 28.94 | 28.86 |

EXAMPLES OF COMPOSITIONS

Example 1

The following composition is prepared:

| | |
|---|---|
| 2,4-Bis-N—β-hydroxyethylamino-5-chloronitrobenzene | 0.1 g |
| 2-N—β-Hydroxyethylamino-5-N,N—bis-β-hydroxyethylaminonitrobenzene | 0.9 g |
| 2-N—Methylamino-5-β,Y-dihydroxypropoxynitrobenzene | 0.2 g |
| 2-Methyl-4-N,N—bis-β-hydroxyethylamino-4'-aminoazobenzene | 0.1 g |
| Celliton Blue extra sold by BASF | 0.1 g |
| 2-N—β-hydroxyethylamino-5-hydroxynitrobenzene | 0.05 g |
| Lauric acid | 1.0 g |
| Oleoyldiethanolamide | 3.0 g |
| 2-Butoxyethanol | 5.0 g |
| Ethomeen 18/60 | 3.5 g |
| Cellosize WP03 | 2.0 g |
| Monoethanolamine q.s. pH 9.5 | |
| Demineralized water q.s. | 100 g |

This composition is applied to dark blond hair including a small percentage of white hair.

After 30 minutes' application and rinsing, the dried hair is uniformly light brown in colour.

Example 2

The following composition is prepared:

| | |
|---|---|
| 2-N—β-hydroxyethylamino-4-amino-5-chloronitrobenzene | 0.055 g |
| 2-N—methylamino-5-N—methyl-N—β-hydroxyethylaminonitrobenzene | 0.1 g |
| Celliton Blue extra sold by BASF | 0.015 g |
| Acetoquinone diazo Black BSNZ sold by ICI Francolor | 0.02 g |
| 2-Amino-4-methyl-5-N—β-hydroxyethylaminonitrobenzene | 0.005 g |
| Lauric acid | 1.0 g |
| Oleoyldiethanolamide | 3.0 g |
| 2-Butoxyethanol | 5.0 g |
| Ethomeen 18/60 | 3.5 g |
| Cellosize WP03 | 2.0 g |
| Monoethanolamine q.s. pH 9.5 | |
| Demineralized water q.s. | 100 g |

This thickened liquid is applied to light blond hair discoloured by sunlight.

A rinse is applied after thirty minutes' application and a revived and uniform light blond shade is obtained.

Example 3

The following composition is prepared:

| | |
|---|---|
| 2,4-Bis-N—β-hydroxyethylamino-5-chloronitrobenzene | 0.2 g |
| 2-N—β-Hydroxypropylamino-5-N,N—bis-β-hydroxyethylaminonitrobenzene monohydrochloride | 3.0 g |
| 2-N—Methylamino-4-β,Y-dihydroxypropoxynitrobenzene | 0.4 g |
| 3-Methoxy-4-β-hydroxyethylaminonitrobenzene | 0.05 g |
| Celliton Blue extra sold by BASF | 0.1 g |
| Acetoquinone dark Blue 5 R sold by PCUK | 0.1 g |
| Acetoquinone diazo Black BSNZ sold by | 0.2 g |

-continued

| | |
|---|---|
| ICI Francolor | |
| Nonylphenol containing 9 moles of ethylene oxide | 8.0 g |
| Lauroyldiethanolamide | 2.0 g |
| 2-Ethoxyethanol | 10.0 g |
| 2-Amino-2-methyl-1-propanol q.s. pH 9 | |
| Demineralized water q.s. | 100 g |

This composition is applied to dark brown hair. After 30 minutes' application, it is rinsed off.
The dried hair is then coloured a brown shade.

Example 4

The following composition is prepared:

| | |
|---|---|
| 2-N—β-Hydroxyethylamino-4-amino-5-bromonitrobenzene | 0.02 g |
| 2-N—β-Aminoethylamino-4-amino-5-chloronitrobenzene | 0.1 g |
| 2-N—Methylamino-5-N,N—bis-β-hydroxyethylaminonitrobenzene | 0.15 g |
| 2-Amino-5-N—methylaminobenzene | 0.01 g |
| Celliton Blue extra sold by BASF | 0.1 g |
| Acetoquinone diazo Black BSNZ sold by ICI Francolor | 0.2 g |
| 2-N—β-Hydroxyethylamino-5-hydroxynitrobenzene | 0.03 g |
| 3-Methoxy-4-β-hydroxyethylaminonitrobenzene | 0.15 g |
| Nonylphenol containing 9 moles of ethylene oxide | 8.0 g |
| Lauroyldiethanolamide | 2.0 g |
| 2-Ethoxyethanol | 10.0 g |
| 2-Amino-2-methyl-1-propanol q.s. pH 9 | |
| Demineralized water q.s. | 100 g |

This composition is applied to naturally brown hair.
After 30 minutes' application, rinsing and drying, the hair is dark brown in shade.

Example 5

The following composition is prepared:

| | |
|---|---|
| 2,4-Bis-N—β-hydroxyethylamino-5-chloronitrobenzene | 0.07 g |
| 2-β-Aminoethylamino-4-β-hydroxyethylamino-5-chloronitrobenzene | 0.03 g |
| 2-β-Diethylaminoethylamino-4-amino-5-chloronitrobenzene | 0.02 g |
| 2-N—Methylamino-5-N—methyl-N—β-hydroxyethylaminonitrobenzene | 0.19 g |
| Celliton Blue extra sold by BASF | 0.03 g |
| Acetoquinone diazo Black BSNZ sold by ICI Francolor | 0.035 g |
| 2-Amino-5-N—β-hydroxyethylaminonitrobenzene | 0.005 g |
| Nonylphenol containing 9 moles of ethylene oxide | 8.00 g |
| Lauroyldiethanolamide | 2.00 g |
| 2-Ethoxyethanol | 10.0 g |
| 2-Amino-2-methyl-1-propanol q.s. pH 9 | |
| Demineralized water q.s. | 100 g |

This composition is applied for 20 minutes to light blond hair. After rinsing and drying, a blond shade is obtained.

Example 6

| | |
|---|---|
| 2,4-Bis-N—β-hydroxyethylamino-5-chloronitrobenzene | 0.07 g |
| 2-N—β-Hydroxyethylamino-5-N,N—bis-β-hydroxyethylaminonitrobenzene | 0.15 g |
| Lauric acid | 1 g |
| Oleoyldiethanolamide | 3 g |
| 2-Butoxyethanol | 5 g |
| Ethomeen 18/60 | 3.5 g |
| Cellosize WP03 from Union Carbide | 2 g |
| 2-Amino-2-methyl-1-propanol q.s. pH 9.5 | |
| Demineralized water q.s. | 100 g |

When applied for 30 minutes to light blond hair, this composition gives it, after rinsing and drying, a homogeneous blond shade.

Example 7

| | |
|---|---|
| 2-N—Methylamino-4-amino-5-fluoronitrobenzene | 0.015 g |
| 2-N—Propylamino-4-amino-5-chloronitrobenzene | 0.05 g |
| 2-Amino-4-N—β-hydroxyethylamino-5-chloronitrobenzene | 0.1 g |
| 2-N—β-Hydroxyethylamino-5-(N—methyl-N—β-hydroxyethyl)aminonitrobenzene | 0.6 g |
| 3-Methoxy-4-β-hydroxyethylaminonitrobenzene | 0.05 g |
| Celliton Blue extra (BASF) | 0.08 g |
| Acetoquinone diazo Black BSNZ (ICI Francolor) | 0.9 g |
| Nonylphenol containing 9 moles of ethylene oxide | 8 g |
| Lauroyl diethanolamide | 2 g |
| Ethyl glycol | 10 g |
| 2-Amino-2-methyl-1-propanol q.s. pH 9 | |
| Demineralized water q.s. | 100 g |

The composition described above is applied to naturally dark blond hair.

Example 8

| | |
|---|---|
| 2,4-3-(Hydroxyethyl)amino-5-chloronitrobenzene | 0.18 g |
| 2-N—β-Hydroxyethylamino-5-N,N—bis-β-hydroxyethylaminonitrobenzene | 0.9 g |
| 2-N—Methylamino-5-β,γ-hydroxypropoxynitrobenzene | 0.2 g |
| 2-Methyl-4-N,N—bis-β-hydroxyethylamino-4'-aminoazobenzene | 0.1 g |
| Celliton Blue extra (BASF) | 0.1 g |
| 2-Amino-5-N—β-hydroxyethylaminonitrobenzene | 0.03 g |
| 2-N—β-Hydroxyethylamino-5-methoxynitrobenzene | 0.01 g |
| Lauric acid | 1 g |
| Oleoyldiethanolamide | 3 g |
| 2-Butoxyethanol | 5 g |
| Ethomeen 18/16 | 3.5 g |
| Cellosize WP03 (Union Carbide) | 2 g |
| Monoethanolamine q.s. pH 9.5 | |
| Demineralized water q.s. | 100 g |

This composition is applied to dark blond hair.
After 30 minutes' application and rinsing, the dried hair is of a uniformly light brown shade.

Example 9

| | |
|---|---|
| 2,4-(2-Hydroxypropyl)amino-5-chloronitrobenzene | 0.12 g |
| 2-N—Methylamino-5-N—methyl-N—β-hydroxyethylaminonitrobenzene | 0.1 g |
| Celliton Blue extra (BASF) | 0.015 g |
| Acetoquinone diazo Black BSNZ (ICI Francolor) | 0.02 g |
| 2-Amino-4-methyl-5-N—β,γ-dihydroxypropylaminonitrobenzene | 0.06 g |
| Lauric acid | 1 g |
| Oleoyldiethanolamide | 3 g |
| 2-Butoxyethanol | 5 g |
| Ethomeen 18/60 | 3.5 g |
| Cellosize WP03 (Union Carbide) | 2 g |
| Monoethanolamine q.s. pH 9.5 | |
| Demineralized water q.s. | 100 g |

This thickened liquid is applied to very light blond hair.

A rinse is performed after 30 minutes' application. A light blond shade is obtained.

The above trade names correspond to the following products:

Ethomeen 18/60: Stearylamine oxyethylenated with 50 moles of ethylene oxide, identified by the CTFA under the name: PEG 50 stearamine, sold by the Armak Company Cellosize WP03: Hydroxyethyl cellulose, sold by the Union Carbide Company

We claim:

1. Dye composition for direct dyeing of keratinic fibres, especially human hair, containing in a cosmetically acceptable medium
(a) a yellow or green-yellow dye corresponding to the formula (I):

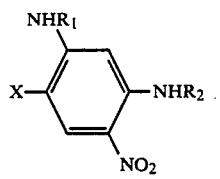

in which X=Cl, Br, F, $R_1$ and $R_2$ denote, independently of each other, hydrogen, alkyl, hydroxyalkyl or alkylaminoalkyl in which the alkylamino group may be mono- or disubstituted, provided that $R_1$ and $R_2$ do not simultaneously denote a hydrogen atom, and
(b) a blue or violet dye corresponding to the formula:

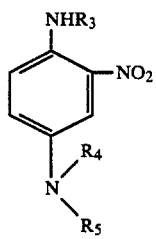

in which $R_3$ denotes a hydrogen atom, an alkyl or monohydroxyalkyl, polyhydroxyalkyl or alkoxyalkyl radical and $R_4$ and $R_5$ have separately the same meanings as $R_3$ but cannot denote a hydrogen atom.

2. Composition according to claim 1 wherein dye of formula (I) is selected from the group consisting of: 2-N-β-hydroxyethylamino-4-N-β-hydroxyethylamino-5-chloronitrobenzene, 2-N-methylamino-4-amino-5-fluoronitrobenzene, 2-N-β-hydroxyethylamino-4-amino-5-chloronitrobenzene, 2-N-propylamino-4-amino-5-chloronitrobenzene, 2-N-β-hydroxyethylamino-4-amino-5-bromonitrobenzene, 2-amino-4-N-β-hydroxyethylamino-5-chloronitrobenzene, 2-N-β-aminoethylamino-4-amino-5-chloronitrobenzene, 2-N-methylamino-4-amino-5-fluoronitrobenzene, 2-β-N,N-diethylaminoethylamino-4-amino-5-chloronitrobenzene, 2-N-β-aminoethylamino-4-hydroxyethylamino-5-chloronitrobenzene 2,4-bis-N-γ-hydroxypropylamino-5-chloronitrobenzene, and 2,4-bis-N-β-hydroxypropylamino-5-chloronitrobenzene.

3. Composition according to claim 1 wherein the blue or violet dyes are selected from the group consisting of: 2-N-methylamino-5-N,N-bis-β-hydroxyethylaminonitrobenzene, 2-N-methylamino-5-(N-methyl-N-β-hydroxyethyl)aminonitrobenzene, 2-N-β-hydroxyethylamino-5-N,N-bis-β-hydroxyethylaminonitrobenzene, 2-(N-β-hydroxyethyl)amino-5-(N-methyl-N-β-hydroxyethyl)aminonitrobenzene, 2-N-β-hydroxypropylamino-5-N,N-bis(β-hydroxyethyl)aminonitrobenzene, 2-N-methylamino-5-(N-methyl-N-β,γ-dihydroxypropyl)aminonitrobenzene, 2-amino-5-N,N-bis(γ-hydroxyethyl)aminonitrobenzene, 2-N-β-hydroxyethylamino-5-(N-ethyl-N-β-hydroxyethyl)aminonitrobenzene, 2-β-methoxyethylamino-5-N,N-bis-β-hydroxyethylaminonitrobenzene and 2-N-β,γ-dihydroxypropylamino-5-(N-methyl-N-β-hydroxyethyl)aminonitrobenzene.

4. Composition according to claim 1 containing additionally nitrobenzene dyes other than the dyes of formula (I) or (II), azo, aminoanthraquinone and metal-containing dyes, triarylmethane derivatives and indoamine dyes.

5. Composition according to claim 1 wherein the cosmetically acceptable medium consists of water or a mixture of water and a solvent chosen from alcohols, glycols or glycol ethers, at concentrations of between 0.5 and 20% by weight.

6. Composition according to claim 1 characterized in that it additionally contains fatty amides in concentrations of between 0.05 and 10% by weight of the total weight of the composition.

7. Composition according to claim 1 containing anionic, cationic, nonionic or amphoteric surfactants or mixtures thereof in proportions of between 0.1 and 50% by weight.

8. Composition according to claim 1 containing thickening agents which are sodium alginate, gum arabic, guar gum, xanthane gum, cellulose derivatives, acrylic acid polymers and inorganic thickeners in proportions of between 0.1 and 5% by weight.

9. Composition according to claim 1 having a pH between 4 and 10.5.

10. Process for dyeing keratinic fibres, especially human hair, comprising the step of applying the composition as defined in claim 1 to the said dry or wet fibres, allowing it to act and drying the fibres.

11. Process for dyeing keratinic fibres, especially human hair, comprising the steps of applying a composition as defined in claim 1 for an application time of between 3 and 60 minutes, rinsing, washing if appropriate, rinsing again and drying.

12. Dye composition for direct dyeing of keratinic fibers, especially human hair, containing in a cosmetically acceptable medium
(a) a yellow or green-yellow dye corresponding to formula (I):

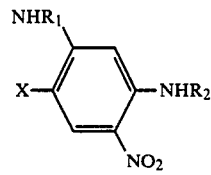

in which X=Cl, Br, F, $R_1$ and $R_2$ denote, independently of each other, hydrogen, alkyl, hydroxyalkyl or alkylaminoalkyl in which the alkylamino group may be mono- or disubstituted, provided that $R_1$ and $R_2$ do not simultaneously denote a hydrogen atom, and (b) a blue or violet dye corresponding to the formula (II):

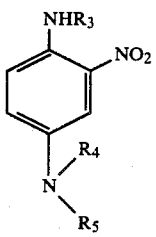

in which $R_3$ denotes a hydrogen atom, an alkyl or monohydroxyalkyl, polyhydroxyalkyl or alkoxyalkyl radical and $R_4$ and $R_5$ have separately the same meanings as $R_3$ but cannot denote a hydrogen atom; the dye formula (I) being present in proportions of between 0.01 and 2% by weight and the dye of formula (II) being present in proportions of between 0.01 and 5% by weight, relative to the total weight of the composition.

13. Dye composition for direct dyeing of keratinic fibers, especially human hair, containing in a cosmetically acceptable medium the yellow dye 2-N-β-hydroxyethylamino-4-N-hydroxyethylamino-5-chloronitrobenzene, in an amount between 0.01 and 2% by weight, and a blue or violet dye corresponding to the formula:

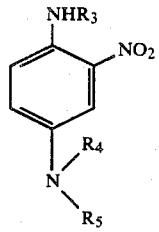

in which $R_3$ denotes a hydrogen atom, an alkyl or monohydroxyalkyl, polyhydroxyalkyl or alkoxyalkyl radical and $R_4$ and $R_5$ have separately the same meaning as $R_3$ but cannot denote a hydrogen atom; said blue or violet dye being present in a proportion of between 0.01 and 5% by weight.

* * * * *